United States Patent [19]

Bolhofer et al.

[11] Patent Number: 4,490,533

[45] Date of Patent: Dec. 25, 1984

[54] AMINOALKYL PYRIDINE DERIVATIVES

[75] Inventors: William A. Bolhofer, Frederick; Jacob M. Hoffman, North Wales, both of Pa.

[73] Assignee: Merck & Co., Inc., Rahway, N.J.

[21] Appl. No.: 306,441

[22] Filed: Sep. 29, 1981

Related U.S. Application Data

[63] Continuation-in-part of Ser. No. 218,606, Dec. 22, 1980, abandoned.

[51] Int. Cl.$^3$ .................. C07D 211/70; C07D 211/82; C07D 213/24; C07D 213/53
[52] U.S. Cl. ..................................... 546/332; 546/334
[58] Field of Search ............................... 546/332, 334

[56] References Cited

U.S. PATENT DOCUMENTS 3,994,905  11/1976  Kilbourn et al. ................... 546/332

Primary Examiner—Henry R. Jiles
Assistant Examiner—Robert C. Whittenbaugh
Attorney, Agent, or Firm—Gabriel Lopez; Salvatore C. Mitri; Hesna J. Pfeiffer

[57]  ABSTRACT

There are disclosed novel compounds described as aminoalkyl pyridine derivatives in which the aminoalkyl pyridine is connected to a guanidine moiety or a functional equivalent thereof, either directly or through a linear connecting group. Processes for the preparation of such compounds are also disclosed. The compounds are useful for the suppression of gastirc acid secretions in mammals and compositions for such uses are also disclosed.

4 Claims, No Drawings

AMINOALKYL PYRIDINE DERIVATIVES

This is a continuation-in-part application of application Ser. No. 218,606 filed Dec. 22, 1980 now abandoned.

BACKGROUND OF THE INVENTION

Imidazolylcyanoguanidines in which the imidazole and cyanoguanidine are joined through a linear connecting group are known as $H_2$ receptor inhibitors. See U.S. Pat. No. 3,950,333 to Durant et al. In addition, compounds have been prepared similar to those of Durant et al. in which the imidazole moiety has been replaced by an alkylaminofuran moiety. See U.S. Pat. No. 4,128,658 to Price et al. The instant compounds differ in utilizing the aminoalkyl pyridine moiety.

SUMMARY OF THE INVENTION

This invention is concerned with aminoalkyl pyridine compounds wherein the aminoalkyl pyridine is connected either directly to a guanidine or guanidine-like moiety, or through a linear connecting group. Thus, it is an object of this invention to describe such compounds. A further object of this invention is to describe processes for the preparation of such compounds. A still further object is to describe the use of such compounds as gastric acid secretion inhibitors in mammals. Further objects will become apparent from a reading of the following description.

DESCRIPTION OF THE INVENTION

The compounds of this invention are best realized in the following structural formula:

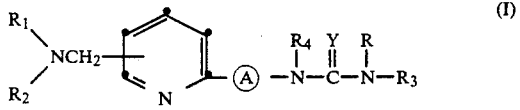

wherein
- $R_1$ and $R_2$ are independently loweralkyl of from 1 to 3 carbon atoms and $R_1$ and $R_2$ may be joined to form, together with the nitrogen atom to which they are attached, a 5- or 6-membered heterocyclic ring, which may optionally contain another heteroatom selected from oxygen or N-$R_5$ wherein $R_5$ is hydrogen or loweralkyl;
- $R_3$ is hydrogen, loweralkyl, cycloloweralkyl; loweralkyl substituted with cycloloweralkyl, loweralkenyl, loweralklynyl, phenylloweralkyl, hydroxyloweralkyl, loweralkoxy, or mono- and di(loweralkyl) aminoloweralkyl;
- Y is oxygen, sulfur, $CHNO_2$ or N-$R_6$ wherein $R_6$ is nitro, cyano or loweralkylsulfonyl,
- $R_4$ is hydrogen or loweralkyl;
- R is hydrogen or loweralkyl;
- Ⓐ is either a single bond connection or —($CH_2$)$_n$—X—($CH_2$)$_m$—;

wherein:
- n is 0 or 1;
- m is 2-4; and
- X is oxygen or sulfur.

In the instant invention, the term "loweralkyl," unless otherwise defined, is intended to include those alkyl groups, of either a straight or branched configuration, which contain from 1-5 carbon atoms. Exemplary of such alkyl groups are methyl, ethyl, propyl, iso-propyl, butyl, sec-butyl, pentyl and the like.

The term "loweralkoxy" is intended to include those alkoxy groups of either straight or branched configuration, which contain from 1-5 carbon atoms. Exemplary of such alkoxy groups are methoxy, ethoxy, propoxy, isopropoxy, butoxy, pentoxy and the like.

The term "loweralkenyl" is intended to include those alkenyl groups, of either a straight or branched configuration, which contain from 3-5 carbon atoms. Exemplary of such alkenyl groups are allyl, butenyl, 1-methyl-2-butenyl, pentenyl, and the like.

The term "loweralkynyl" is intended to include those alkynyl groups of either straight or branched configuration which contain from 3-5 carbon atoms. Exemplary of such alkynyl groups are propargyl, butynyl, pentynyl, and the like.

The term "cycloloweralkyl" is intended to include those cycloalkyl groups which contain from 3-6 carbon atoms. Exemplary of such groups are cyclopropyl, cyclobutyl, cyclopentyl and cyclohexyl.

The heterocycle formed by joining $R_1$ and $R_2$ may be piperidine, pyrrolidine, morpholine, piperazine, N-methyl piperazine and the like.

The preferred compounds of the instant invention are realized in the above structural formula wherein $R_1$ and $R_2$ are the same and are loweralkyl of from 1 to 3 carbon atoms;
- $R_3$ is hydrogen, loweralkyl, or lower-alkynyl;
- Y is oxygen, sulfur, $CHNO_2$ or N—CN; and
- R, $R_4$ and Ⓐ are as defined above.

Further preferred compounds are realized when:
- $R_1$ and $R_2$ are methyl;
- $R_3$ is methyl, ethyl or propargyl;
- Y is oxygen, sulfur, CH—$NO_2$ or N—CN, and
- R, $R_4$ and Ⓐ are as defined above.

The most preferred compounds are those wherein:
- $R_1$ and $R_2$ are methyl;
- $R_3$ is methyl;
- Y is oxygen, sulfur, CH—$NO_2$ or N—CN; and
- R, $R_4$ and Ⓐ are as defined above.

The compounds according to the invention readily form physiologically acceptable salts. Such salts include salts with inorganic and organic acids such as hydrochlorides, hydrobromides and sulfates. Particularly useful salts of organic acids are formed with aliphatic mono- or di-carboxylic acids. Examples of such salts are acetates, maleates and fumarates. The compounds may also form hydrates.

The compounds according to the invention can be administered orally, topically or parenterally or by suppository, of which the preferred route is the oral route. They may be used in the form of the base or as a physiologically acceptable salt. They will in general be associated with a pharmaceutically acceptable carrier or diluent, to provide a pharmaceutical composition.

The compounds according to the invention can be administered in combination with other active ingredients, e.g. conventional antihistamines if required. For oral administration the pharmaceutical composition can most conveniently be in the form of capsules or tablets, which may be slow release tablets. The composition may also take the form of a dragee or may be in the syrup form. Suitable topical preparation include ointments, lotions, creams, powders and sprays.

A convenient daily dose by the oral route would be of the order of 100 mg. to 1.2 g. per day, in the form of dosage units containing from 20 to 200 mg. per dosage unit. A convenient regimen in the case of a slow release tablet would be twice or three times a day.

Parenteral administration may be by injection at intervals or as a continuous infusion. Injection solutions may contain from 10 to 100 mg./ml of active ingredient.

The compounds of the present invention may be made by reacting a primary amine of the formula:

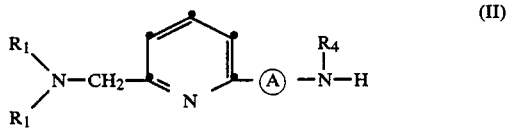
(II)

wherein $R_1$ and $R_2$, $R_4$ and Ⓐ are as defined above with a compound capable of introducing directly or indirectly the group:

wherein R, $R_3$ and Y have the meanings given herein.

Compounds capable of introducing compounds wherein Y is oxygen or sulfur and R, and $R_3$ are hydrogen are cyanates or thiocyanates, preferably alkali metal cyanates or thiocyanates.

When R is hydrogen, $R_3$ is alkyl and Y is oxygen or sulfur, isocyanates or isothiocyanates are used.

When R and $R_3$ are both alkyl and Y is oxygen or sulfur, carbamoylchlorides, or thiocarbamoylchlorides are used.

In the foregoing cases the amine and the reactant are allowed to stand in a solvent such as acetonitrile at ambient or elevated temperatures.

Other compounds capable of introducing the foregoing group wherein R is hydrogen are

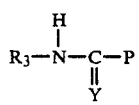

wherein P is a leaving group and Y is N-$R_6$ or CH—NO$_2$. The reaction between the amine (II) and

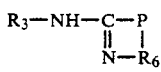

may be carried out in a solvent such as ethanol or acetonitrile at ambient or elevated temperatures in the presence of silver nitrate as required.

The reaction between the amine (II) and the compound

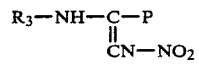

is carried out by stirring in solvents such as ethanol or acetonitrile at ambient or elevated temperatures.

Examples of leaving groups are halogen, methylthio or alkoxy, preferably methylthio.

The introduction of the group:

may also be effected indirectly by first reacting the amine (II) with a compound of the formula:

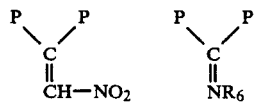

in which P is a leaving group as defined above. This reaction may be effected in a solvent, e.g. ether or acetonitrile at a temperature from ambient to reflux. Treatment of the resulting compound of formula (III):

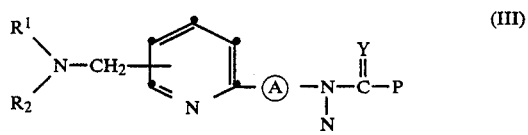
(III)

where Y represents =NR$_4$ or =CH—NO$_2$ with a primary amine R$_3$NH$_2$ at a temperature from ambient to reflux gives the desired end product (I).

The preferred compounds of this invention wherein Y is oxygen or sulfur are prepared by reacting the appropriately substituted amine of structure II with an appropriately substituted carbamoylchloride. The reaction is carried out in an inert, aprotic solvent such as benzene or toluene, and is complete in from 4 to 24 hours at from room temperature to the reflux temperature of the reaction mixture. It is preferable to include a base in the reaction mixture, such as a tertiary amine, to react with the liberated hydrogen halide. The product is isolated using known techniques.

The preferred compounds of this invention wherein Y is a nitromethylene group (=CHNO$_2$) or a cyanoimino group (=N—CN) are prepared according to the following reaction scheme:

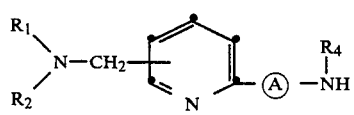
(II)

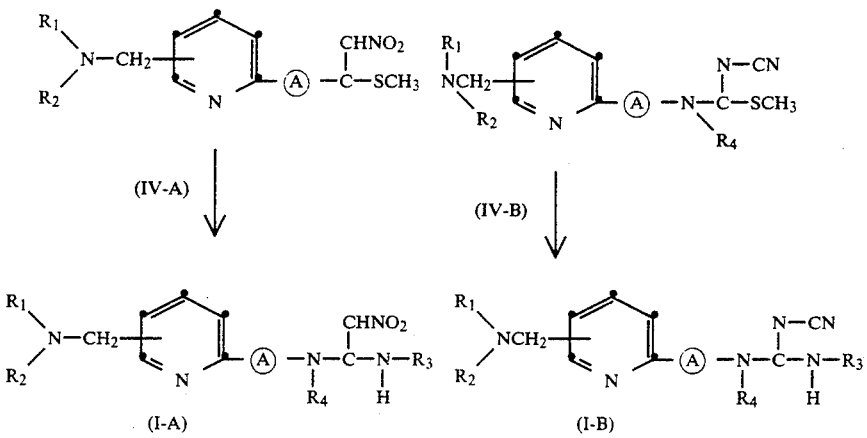

(I-A)
(I-B)

wherein $R_1$, $R_2$, $R_3$, $R_4$ and Ⓐ are as defined above.

In the first step of the reaction for the preparation of the nitromethylene compound (I-A), the amine starting material (II) is treated with 1,1-bis-methylthio-2-nitroethene in a suitable solvent, preferably acetonitrile or a lower alcohol, such as ethanol. The reaction may be carried out at about 20° C. to the reflux temperature of the reaction mixture. The reaction is substantially complete in about 8 hours to several days. It is preferred to stir the reaction mixture overnight at about 55°–60° C.

In the first step of the reaction for the preparation of the cyanoimino compound (I-B) the amine starting material (III) is reacted with dimethyl cyano dithioimidocarbonate in a suitable solvent, preferably acetonitrile or a lower alcohol, such as ethanol. The reaction may be carried out at about 20° C. to the reflux temperature of the reaction mixture. The reaction is substantially complete in about 1 hour to several days. It is preferred to stir the reaction mixture overnight at about room temperature.

The next step of this reaction sequence is the same for Compounds IV-A and IV-B and involves the displacement of the methylthio group of Compound IV-A and IV-B by a loweralkylamino group. A loweralkyl amine is employed and the reaction is carried out by dissolving the amine in a solvent, such as a lower alcohol, preferably ethanol. The reaction is carried out at from 0° C. to the reflux temperature of the reaction mixture. However, where volatile amines are employed the reaction mixture must either be maintained at from 0° C. to room temperature or, if heating is required, the reaction must be placed in a sealed reaction vessel. It is preferred to use atmospheric pressure for the reaction, and to keep the temperature at about room temperature or less. The reaction is complete in about 1 hour to several days, with most reactions requiring stirring overnight. The products (I-A and I-B) are isolated using techniques known to those skilled in this art.

In the foregoing reaction scheme wherein Ⓐ is a single bond connection and Y is the cyanoimino group, that is compounds I-B, a variation in the process for the preparation of the intermediate IV-B is required. In order to successfully react the amine II with dimethyl cyanodithiomidocarbonate, an anion of compound II must be prepared. This is accomplished by reacting the amine starting material with a strong base, such as sodium hydride. The reaction is carried out in an aprotic solvent such as benzene or toluene. When sodium hydride is employed, the reactants are refluxed for from ½ to 4 hours before the addition of the dimethylcyanodithiomidocarbonate. For the most efficient conversion two equivalents of the sodium hydride are employed for each equivalent of the amine compound (II).

The amine intermediates (II) are prepared by reacting an appropriately substituted halopyridine or halomethylpyridine (V) with hydroxy or mercapto substituted alkylamine.

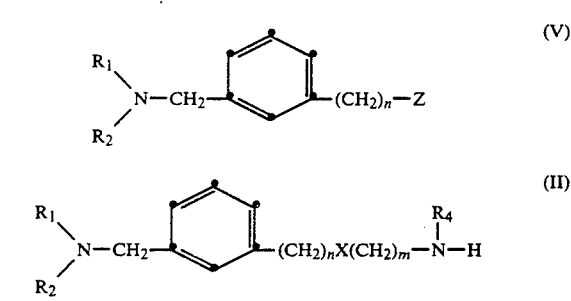

wherein:

$R_1$, $R_2$, n, m and $R_4$ are as defined previously, and

Z is a halogen, preferably chlorine or bromine.

The reaction is carried out by first preparing the alkalinate salt of the hydroxy or mercapto substituted alkylamine with a base such as sodium hydride. The reaction is generally started at about room temperature in an aprotic solvent such as dimethylformamide. When the temperature is raised to about 80°–150° C. the halogenated pyridine compound (V) is added dropwise. The reaction mixture is then heated for from 1 to 4 hours. The intermedite (II) is then isolated using standard techniques known to those skilled in the art. In the case where X is oxygen it has been found that the formamido group is formed at the terminal amine which must be hydrolized with sodium or potassium hydroxide in an alcohol at reflux for 10–40 hours. The resultant amine is isolated using known techniques.

The following examples are provided in order that the invention might be more fully understood. They are not to be construed as limitative of the invention.

EXAMPLE 1

N-Cyano-N'-methyl'N''-(6-dimethylaminomethyl-2-pyridyl)Guanidine

A. 6-Bromomethyl-2-phthalimido pyridine

A mixture of 6-methyl-2-phthalimido pyridine (17.5 gm, 73.5 mmol) and N-bromo succinimide (15.7 gm, 88 mmol) in carbon tetrachloride (275 ml) containing 100 mg of benzoyl peroxide is heated at reflux for 21 hours. The reaction is filtered hot to remove succinimide (8.3 gm) and cooled. The product is collected and dried affording 13.6 gm of 6-bromomethyl-2-phalimido pyridine which can be recrystallized from chloroform/carbon tetrachloride affording material with a melting point of 168°–170° C. Evaporation of the filtrate yields 7.4 gm of starting material.

B. 6-Dimethylamino-2-amino pyridine

To ethanol (140 ml) saturated with dimethylamine gas at ice bath temperature is added 6-bromomethyl-2-phthalimido-pyridine (13.6 gm, 43 mmol). After stirring for 2 hours, the solution is concentrated to half volume to remove any excess dimethylamine. Hydrazine hydrate (2.4 ml) is added and refluxed for 2 hours. The reaction is cooled, filtered to remove precipitated by-product and evaporated to dryness. The residue is dissolved in chloroform, washed with water, dried over anhydrous sodium sulfate, filtered and evaporated to give 3.8 gm of 6-dimethylamino-2-amino pyridine as an oil.

C. N-Cyano-N'-(6-dimethylaminomethyl-2-pyridyl)-S-methylisothiourea

To a solution of 6-dimethylaminomethyl-2-aminopyridine (2.0 gm, 13.4 mmol) in dry toluene (35 ml) is added 50% sodium hydride in mineral oil (1.3 gm, 27.0 mmol). The reaction mixture is heated at reflux for one hour, cooled to room temperature and dimethyl cyanodithiomido carbonate (2.0 gm) is added. The reaction mixture is warmed to 100° C. for one hour. The reaction is cooled, extracted with water, and the water layer is acidified with acetic acid. The product is extracted with methylene chloride, which is dried and evaporated to give 2.0 gm of N-cyano-N'-(6-dimethylaminomethyl-3-pyridyl)-S-methylisothiourea.

D. N-Cyano-N'-methyl-N''-(6-dimethylaminomethyl-2-pyridyl)guanidine

N-Cyano-N'-(6-dimethylaminomethyl-2-pyridyl)-S-methyl isothiourea (3.0 gm, 12.0 mmol) is dissolved in ethanol (45 ml), cooled in ice bath and saturated with methylamine gas. The reaction is stirred with gradual warming to room temperature for 12 hours. The solvent is evaporated and residue is chromatographed on silica gel (100 gm) eluting with 3–6% methanol/chloroform to give 1.5 gm of product. Recrystallization from acetonitrile gave 1.1 gm of N-cyano-N'-methyl-N''-(6-dimethylaminomethyl-2-pyridyl) guanidine, m.p. 180°–181° C.

EXAMPLE 2

N,N,N'-Trimethyl-N'-(6-dimethylaminomethyl-2-pyridyl) Urea Hydrochloride Hemihydrate

A. 2-Chloro-6-dimethylaminomethylpyridine

2-Chloro-6-methylpyridine (6.4 g, 0.05 mol) is refluxed with N-bromosuccinimide (8.9 g, 0.05 mol) in 50 ml of carbon tetrachloride with benzoyl peroxide (50 mg) until the N-bromosuccinimide has reacted completely (7-14 hours). The succinimide is removed by filtering and the filtrate is saturated with anhydrous dimethylamine. Dimethylamine hydrochloride is removed by filtration and the filtrate is concentrated in vacuo. The residual oil is taken up in hexane and extracted into dilute hydrochloric acid. After the acid extract is washed with ether it is made basic with sodium hydroxide and extracted with ether. The ether extract is dried over anhydrous sodium sulfate, filtered and concentrated in vacuo. This gives 2.2 g of 2-chloro-6-dimethylaminomethylpyridine as a pale yellow oil.

B. 6-Dimethylaminomethyl-2-methylaminopyridine

2-Chloro-6-dimethylaminomethylpyridine (6.8 g, 0.04 mol), methylamine (12.0 g, 0.32 mole) and ethanol (25 ml) are heated at 180°–200° C. for 36 hours in a sealed reaction vessel. The solvent is removed in vacuo and the residue is made basic with excess sodium hydroxide and extracted with ether. The ether extract is dried over anhydrous sodium sulfate, filtered and concentrated in vacuo. This gives 5.8 g of amber oil. The oil is distilled at 90°–100° C. at 1.8 mm and is further purified by chromatography. This gives 2.7 g of 6-dimethylaminomethyl-2-methylaminopyridine as a colorless oil.

C. N,N,N'-Trimethyl-N'-(6-dimethylaminomethyl-2-pyridyl)urea Hydrochloride Hemihydrate To 2-dimethylaminomethyl-6-methylaminopyridine (2.14 g, 0.013 mol) in dry benzene (35 ml) is added triethylamine (1.77 g, 0.0175 mol) and dimethylcarbamoyl chloride (1.72 g, 0.016 mol). The solution is stirred under nitrogen at reflux for 16 hours overnight. The mixture is cooled to room temperature and filtered. The filtrate is concentrated in vacuo and the residual oil is taken up in ether, filtered and again concentrated in vacuo. The residual oil is converted to the monohydrochloride salt with 6N ethanolic hydrochloric acid (1.7 ml, 0.0103 mol). The solid is recrystallized from ethanol-ether sever..1 times, affording 2.2 g of N,N,N'-trimethyl-N'-(6-dimethylaminomethyl-2-pyridyl)urea hydrochloride hemihydrate as a white solid, m.p. 154°–155° C.

EXAMPLE 3

N-Cyano-N'-{2-[(6-dimethylaminomethyl-2-pyridyl)methylthio]ethyl}-N''-methylguanidine

A. 6-Dimethylaminomethyl-2-[(2-phthalimidoethyl)thiomethyl]pyridine

To a solution of N-(2-mercaptoethyl) phthalimide (28.8 g, 0.139 mol) in dry methanol (250 ml) is added sodium methoxide (7.5 g, 0.139 mol) with cooling and stirring. This mercaptide solution is added to 2,6-bis(-chloromethyl)pyridine (24.5 g, 0.139 mol) in dry methanol (250 ml). The mixture is stirred at room temperature for 2½ hours and is filtered to remove the precipitated solid. Then dimethylamine (6.9 g, 0.153 mol) in cold methanol (150 ml) is added to the filtrate and the mixture is stirred at room temperature overnight. The solvent is removed in vacuo leaving an amber gum. The gum is taken up in methylene chloride (200 ml) and is washed with aqueous sodium bicarbonate and with water. The methylene chloride layer is dried over anhydrous sodium sulfate, filtered and concentrated in vacuo. This gives 24.3 g of 6-dimethylaminomethyl-2-[(2-phthalimidoethyl)thiomethyl]pyridine as a crude amber gum.

B.
2-[(2-Aminoethyl)thiomethyl]-6-dimethylaminomethyl pyridine

6-Dimethylaminomethyl-2-[(2-phthalimidoethyl) thiomethyl]pyridine (24.3 g, 0.068 mol) is dissolved in methanol (150 ml) and hydrazine hydrate (4.8 g, 0.087 mol) is added. The solution is refluxed for 1½ hours and is concentrated in vacuo. The solid residue is dissolved in water (250 ml) 12N HCl (35 ml) is added and the mixture is cooled and filtered. The filtrate is washed with chloroform and concentrated in vacuo. The residue is basified with excess sodium bicarbonate and concentrated to dryness in vacuo. The solid residue is extracted with chloroform/methanol (50/50) (200 ml) and the extract is dried over anhydrous sodium sulfate, filtered and concentrated in vacuo. This gives 10.3 g of 2-[(2-aminoethyl)thiomethyl]-6-dimethylaminomethyl pyridine as a light amber oil.

C.
N-Cyano-S-Methyl-N¹-[2-[(6-Dimethylaminomethyl-2-pyridyl)methylthio]ethyl]Isothiourea 2-(2-Aminoethylthiomethyl)-6-dimethylaminomethyl pyridine (10.2 g, 0.0453 mol) is dissolved in 30 ml of ethanol and dimethyl cyanodithioimidocarbonate (6.62 g, 0.0453 mol) is added. The solution is stirred under nitrogen for 16 hours at room temperature. The resulting mixture is diluted with excess ether and is filtered to obtain 9.6 g of N-cyano-S-methyl-N¹-[2-[(6-dimethylaminomethyl-2-pyridyl)methylthio]ethyl]Isothiourea.

D.
N-Cyano-N'-{2-[(6-dimethylaminomethyl-2-pyridyl)methylthio]ethyl}-N"-methylguanidine A sample of N-cyano-S-methyl-N¹-[2-[(6-dimethylaminomethyl-2-pyridyl)methylthio]ethyl]Isothiourea (4.4 g, 0.0137 mol) is suspended in 20 ml of ethanol containing methylamine (1.7 g, 0.0548 mol) and the mixture is stirred at room temperature overnight. The resulting solution is concentrated in vacuo to an amber oil (3.5 g) which is twice chromatographed on neutral aluminum oxide using chloroform. N-cyano-N'-{2-[(6-dimethylaminomethyl-2-pyridyl)methylthio]ethyl}-N"-methylguanidine is obtained as a nearly colorless oil (1.8 g).

EXAMPLE 4

N-[3-(6-Dimethylaminomethyl-2-pyridylthio)propyl]-N'-methyl-2-nitro-1,1-diaminoethene

A.
3-(6-Dimethylaminomethyl-2-pyridylthio)propylamine

A mixture of 3-mercaptopropylamino (4.8 g, 0.053 ml) and 60% sodium hydride in mineral oil (2.18 g, 0.054 mol) in dry dimethylformamide (50 ml) is heated to 80° C. and a solution of 6-dimethylaminomethyl-2-chloropyridine (8.7 g, 0.051 mol) in 50 ml of dry DMF is added dropwise. The mixture is heated at 125° C. for 3 hours, cooled and diluted with ethanol (70 mol). After filtration to remove precipitated salts, the filtrate is evaporated to dryness. This residue is dissolved in water and the product is extracted into chloroform, then into dilute hydrochloric acid and the acidic extract is neutralized with sodium carbonate. The product is extracted into chloroform, dried and evaporated to give 9.5 g. This residual oil is distilled to give 5.64 g of pure product, bp: 129°–133° C./0.5 mm.

B.
1-[3-(6-Dimethylaminomethyl-2-pyridylthio)-propylamino]-1-methylthio-2-nitroethene A mixture of 3-(6-dimethylaminomethyl-2-pyridylthio)-propylamine (1.13 g, 0.005 mol) and 1,1-bis(methylthio)-2-nitroethene (0.86 g, 0.0052 mol) in acetonitrile (10 ml) is warmed briefly to effect solution and then allowed to stand at ambient temperature for 18 hours. The solvent is evaporated and the residue is chromotographed on silica gel (50 g) eluting with 3–7% methanol/chloroform to give 1.25 g of a glassy product.

C.
N-[3-(6-Dimethylaminomethyl-2-pyridylthio)propyl]-N'-methyl-2-nitro-1,1-diaminoethene 1-[3-(6-Dimethylaminomethyl-2-pyridylthio)propylamino]-1-methylthio-2-nitroethene (1.25 g, 0.0037 mol) is added to ethanol (15 ml) saturated with monomethylamine gas at ice bath temperature and is allowed to stir at ambient temperature for 18 hours. The reaction solvent is removed and the residue is chromatographed on silica gel (50 g) eluting with 5–20% methanol/chloroform to 1.1 g of a glassy product.

EXAMPLE 5

N-[2-(6-Dimethylaminomethyl-2-pyridylthio)ethyl]-N'-methyl-2-nitro-1,1-diaminoethene

A.
2-(6-Dimethylaminomethyl-2-pyridylthio)ethylamine

Cysteamine hydrochloride (3.43 g, 0.030 mol) is added to a suspension of 60% sodium hydride in mineral oil (2.5 g, 0.0625 mol) in dry dimethylformamide (30 ml) and is warmed to 80° C. A solution of 6-dimethylaminomethyl-2-chloropyridine (5.0 g, 029.4 mol) in 30 ml of dry dimethylformamide is added dropwise and the reaction temperature is increased to 125° C. for 2 hours. The reaction is cooled, diluted with ethanol (60 ml) and the salts are removed by filtration before evaporating to dryness. This residue is dissolved in chloroform, washed with water and extracted into dilute hydrochloric acid. The acidic extract is neutralized with sodium carbonate and the product is extracted into chloroform, dried and evaporated to give 4.4 g. This residual oil is distilled to give 2.74 g of pure product, bp: 109°–114° C./0.25 mm.

B.
1-[2-(6-Dimethylaminomethyl-2-pyridylthio)ethylamine]-1-methylthio-2-nitroethene A mixture of 2-(6-dimethylaminomethyl-2-pyridylthio)-ethylamine (0.60 g, 0.0029 mol) and 1,1-bis(methylthio)-2-nitroethene (0.65 g, 0.0039 mol) in acetonitrile (5 ml) is warmed briefly to effect solution and stirred at ambient temperature for two days. The solvent is evaporated and the residue is chromatographed on silica gel (50 g) eluting with 2–10% methanol/chloroform to give 0.55 g of pure product which slowly crystallized, mp: 79–81° C.

C.
N-[2-(6-Dimethylaminomethyl-2-pyridylthio)ethyl]-N'-methyl-2-nitro-1,1-diaminoethene 1-[2-(6-Dimethylaminomethyl-2-pyridylthio)ethylamino]-1-methylthio-2-nitroethene (0.45 g, 0.0014 mol) is added to ethanol (8 ml) saturated with monomethylamine gas at ice bath temperature and is allowed to stir at ambient temperature for 18 hours. Evaporation of the solvent yielded a glassy product.

EXAMPLE 6

N-[3-(6-Dimethylaminomethyl-2-pyridyloxy)propyl]-N'-methyl-2-nitro-1,1-diaminoethene A.
N-[3-(6-Dimethylaminomethyl-2-pyridyloxy)propyl]-formamide 3-Aminopropanol (2.55 g, 0.034 mol) is added to a suspension of 60% sodium hydride in mineral oil (1.29 g, 0.033 mol) in dry dimethylformamide (30 ml) and the mixture is warmed to 80° C. before adding dropwise a solution of 6-dimethylaminomethyl-2-chloropyridine (5.45 g, 0.032 mol) in 30 ml of dry dimethylformamide. The reaction temperature is increased to 125° C. for 3 hours. Then the reaction is cooled, diluted with ethanol and the precipitated salts filtered. The solvents are removed under vacuum. The residue is dissolved in chloroform, washed with water, extracted into dilute hydrochloric acid and the acidic extract neutralized with sodium carbonate. The crude product is extracted into chloroform dried and evaporated (7.6 g). This residue is chromatorgrphed on silica gel (200 g) eluting with 3–8% methanol/chloroform to give 3.2 g of pure product as an oil.

B.
3-(6-Dimethylaminomethyl-2-pyridyloxy)propylamine

N-[3-(6-Dimethylaminomethyl-2-pyridyloxy) propyl]-formamide (2.7 g, 0.013 mol) is added to a solution of 85% potassium hydroxide pellets (3.0 g) dissolved in methanol (30 ml) and heated at gentle reflux for 21 hours. The reaction is cooled, diluted with diethyl ether (30 ml), the precipitated salts filtered, and the solvent removed under vacuum. The residue is dissolved in water and the product exhaustively extracted into ethanol/chloroform, dried and evaporated to give 2.1 g of pure product.

C.
N-[3-(6-Dimethylaminomethyl-2-pyridyloxy)propyl]-N'-methyl-2-nitro-1,1-diaminoethene Following the procedure of Example 5B and C using 3-(6-dimethylaminomethyl-7-pyridyloxyl propylamine, there is obtained N-[3-(6-dimethylaminomethyl-2-pyridyloxy)propyl]-N'-methyl-2-nitro-1,1-diaminoethene.

What is claimed is:
1. A compound having the formula:

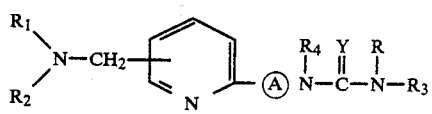

wherein $R_1$ and $R_2$ are independently loweralkyl of from 1 to 3 carbon atoms;

$R_3$ is hydrogen, loweralkyl, cycloloweralkyl; loweralkyl substituted with cycloloweralkyl, loweralkenyl, loweralklynyl, phenylloweralky, hydroxyloweralkyl, loweralkoxy, or mono- and di-(loweralkyl) aminoloweralkyl;

Y is oxygen, or sulfur,

Ⓐ is $-(CH_2)_n-X-(CH_2)_m-$;

wherein:
n is 0 or 1;
m is 2–4;
X is oxygen or sulfur
$R_4$ is hydrogen or loweralkyl;
R is hydrogen or loweralkyl; and the pharmaceutically acceptable salts thereof.

2. The compound of claim 1 wherein $R_1$ and $R_2$ are the same and are loweralkyl of from 1 to 3 carbon atoms;
$R_3$ is hydrogen, loweralkyl or loweralkynyl;
Y is oxygen or, sulfur, and
$R_4$, R are and Ⓐ as defined in claim 1.

3. The compound of claim 2 wherein:
$R_1$ and $R_2$ are methyl;
$R_3$ is methyl, ethyl or propargyl;
Y is oxygen or, sulfur, and
$R_4$, R and Ⓐ are as defined in claim 2.

4. The compound of claim 3 wherein:
$R_1$ and $R_2$ are methyl
$R_3$ is methyl;
Y is oxygen or, sulfur; and
$R_4$, R and Ⓐ as defined in claim 3.

* * * * *